(12) United States Patent
Kieturakis (10) Patent No.: US 10,251,704 B2
(45) Date of Patent: Apr. 9, 2019

(54) SINGLE PORT LAPAROSCOPIC ACCESS SYSTEM WITH EXTERNAL TOOL SUPPORT

(71) Applicant: Maciej J. Kieturakis, Los Altos Hills, CA (US)

(72) Inventor: Maciej J. Kieturakis, Los Altos Hills, CA (US)

( * ) Notice: Subject to any disclaimer, the term of this patent is extended or adjusted under 35 U.S.C. 154(b) by 813 days.

(21) Appl. No.: 14/491,990

(22) Filed: Sep. 20, 2014

(65) Prior Publication Data

US 2016/0081752 A1 Mar. 24, 2016

(51) Int. Cl.

| A61B 1/32 | (2006.01) |
|---|---|
| A61B 19/00 | (2006.01) |
| A61B 17/29 | (2006.01) |
| A61B 17/34 | (2006.01) |
| A61B 17/00 | (2006.01) |
| A61B 90/50 | (2016.01) |

(52) U.S. Cl.
CPC ............ *A61B 19/22* (2013.01); *A61B 17/29* (2013.01); *A61B 17/3423* (2013.01); *A61B 90/50* (2016.02); *A61B 2017/00738* (2013.01); *A61B 2017/00991* (2013.01); *A61B 2017/2902* (2013.01); *A61B 2017/2904* (2013.01); *A61B 2017/2905* (2013.01)

(58) Field of Classification Search
CPC ............... A61B 17/3423; A61B 17/02; A61B 17/0293; A61B 2017/2808; A61B 2017/00991; A61B 17/28–17/29; A61B 2017/00738; A61B 2017/2902; A61B 2017/2906; A61B 2017/2908

USPC .................. 606/129–130, 206; 600/231–233
See application file for complete search history.

(56) References Cited

U.S. PATENT DOCUMENTS

| 3,965,890 | A | 6/1976 | Gauthier | |
| 6,558,407 | B1 * | 5/2003 | Ivanko | F16M 11/40 |
| | | | | 606/130 |
| 2007/0049966 | A1 | 3/2007 | Bonadio et al. | |
| 2010/0113886 | A1 * | 5/2010 | Piskun | A61B 17/3421 |
| | | | | 600/231 |
| 2010/0286671 | A1 | 11/2010 | Person | |
| 2012/0116362 | A1 * | 5/2012 | Kieturakis | A61B 17/29 |
| | | | | 606/1 |
| 2012/0253131 | A1 * | 10/2012 | Malkowski | A61B 17/3421 |
| | | | | 600/201 |

OTHER PUBLICATIONS

International search report and written opinion dated Dec. 11, 2015 for PCT/US2015/051274.

\* cited by examiner

*Primary Examiner* — Zade Coley
*Assistant Examiner* — Jessica Weiss
(74) *Attorney, Agent, or Firm* — Wilson Sonsini Goodrich & Rosati (57) ABSTRACT

A system for performing single port laparoscopic procedures includes a deployment frame and a plurality of tools. The tools are pivotally mounted on the frame and have end effectors which are translatably and rotatably disposed in the tool. A handle at the proximal end of the tool controls an end effector at the distal end of the tool. Movement of the tools relative to the frame is constrained so that they remain in a fixed geometric relationship which prevents the tools from interfering with each other during laparoscopic procedures.

19 Claims, 6 Drawing Sheets

SINGLE PORT LAPAROSCOPIC ACCESS SYSTEM WITH EXTERNAL TOOL SUPPORT

BACKGROUND OF THE INVENTION

1. Field of the Invention

The present invention relates generally to medical systems, tools, and methods. More particularly, the present invention relates to systems and tools for single port laparoscopic access, typically for access through incisions or the umbilicus.

2. Description of the Background Art

In recent years, many open surgical procedures performed in the abdominal cavity have been replaced by minimally invasive procedures performed through several very small incisions using an endoscope, referred to as a laparoscope, inserted through one of the incisions. The other incisions are used for introducing surgical tools, and the abdominal cavity is inflated to create a space for performing the surgery. Such procedures are commonly called "laparoscopic", and can be used for gallbladder removal, hernia repair, hysterectomy, appendectomy, gastric fundoplication, and other procedures. Similar endoscopic, thoracoscopic and other procedures are performed in other body cavities without inflation.

While a great advance over open surgical procedures, which can require an incision of several inches or more through the abdominal wall, such laparoscopic procedures still require incisions through muscle or fascia in several separate sites. Each incision may increase the risk of infection, bleeding trocar site hernia, increased postoperative pain, compromised cosmetic result and other adverse events for the patient.

As an improvement over such laparoscopic procedures, "single port" laparoscopy has been proposed where a single access port is inserted through the umbilicus (the patient's navel). Access solely through the umbilicus is advantageous since it provides a superior cosmetic result. Introducing the laparoscope and all other tools necessary for the surgery through a single port, however, makes performance of the procedures more difficult. In particular, the use of conventional laparoscopic tools, which are typically straight, makes it difficult to approach a single target area in the treated tissue with two or more tools at the same time.

A further improvement in the field of single port laparoscopic surgery is described in U.S. Patent Publication 2012/0116362, commonly assigned with the present application. A system for performing single port laparoscopic procedures includes a transcutaneous seal and a plurality of tools. The tools comprise a substantially rigid tubular seal having a core which is translatably and rotatably disposed in the sleeve. The handle at the proximal end of the tool controls an end effector at the distal end of the tool. The sleeves of the tools are locked in the transcutaneous seals so that they remain in a fixed geometric relationship which prevents the tools from interfering with each other during laparoscopic procedures. While functional and a significant advance in the art, mounting of the tools within the transcutaneous seal can be a challenge.

Thus, it would be a benefit to provide further improved systems and tools for laparoscopic access through single ports for performing minimally invasive surgical procedures. It would be particularly desirable if the tools and other system components were able to facilitate access to target sites and reduce the likelihood that the tools would interfere with each other during the performance of the procedures. In particular, such tools and systems should further allow the physician to intuitively manipulate the tools, while viewing the procedure on the video display, in a manner similar to performance using more conventional multi-port laparoscopy procedures. Still further, such laparoscopic access systems should provide improved structures and methods for supporting the tools relative to the transcutaneous seal with minimum interference and maximum open port area. At least some of these objectives will be met by the inventions described hereinafter.

SUMMARY OF THE INVENTION

In a first aspect of the present invention, a laparoscopic tool system comprises a frame having a periphery and a central opening in a horizontal plane. The frame is configured to be positioned over a transcutaneous incision, such as an incision in a patient's abdomen, typically an umbilicus. First and second tools are pivotally attached at first and second locations on an exterior surface of the frame, typically on a periphery of the frame, respectively. A mid-portion of each tool passes through the central opening of the frame, and the tools are attached to the frame so that they each pivot in at least two vertical planes relative to the frame. In particular, the mid-portion of each tool is positioned to avoid interference between the tools as the tools are pivoted in said at least two vertical planes.

In specific embodiments, the frame comprises a continuous periphery surrounding the central opening, typically a circular ring. Each tool usually has proximal and distal sections which lay along a common axis which passes outside (or in some cases inside) the periphery of the frame. The frame may have variety of sizes so the axes of the proximal and distal sections of the tool may pass outside or within the frame. The distal and proximal sections are typically configured to telescope to accommodate extension and retraction of the actuator and effector, and the mid-portions of each tool are preferably semi-circular and extend radially inwardly from the common axis of the proximal and distal sections.

The tools may be constructed generally as described in in U.S. Patent Publication 2012/0116362, the full disclosure of which is incorporated herein by reference, particularly as illustrated in FIGS. 11-16. The tools in the present invention, however, do not require the receiving tubes which allow direct coupling of the tools to each other as taught by the prior patent publication. In the present invention, at least one tool will include an effector at a distal end thereof, an actuator at a proximal end thereof, and a core passing therethrough which mechanically couples the actuator to the effector so that the actuator may be extended and retracted relative to the mid-portion to extend and retract the effector.

In a second aspect of the present invention, a laparoscopic tool system comprises a transcutaneous incision seal having one end configured to reside on an interior side of an incision, a second end configured to reside on an exterior side of the incision, and sheath extending between the ends to protect the incision. A ring has a central opening, a lower surface, and an exterior periphery, wherein the lower surface is configured to removably attach to the second end of the transcutaneous incision seal. A first rocking attachment block is attached to pivot about a first horizontal axis through the ring, and a first vertical support arm is attached to pivot about a second horizontal axis through the first rocking attachment block. A second rocking attachment block is attached to pivot about a third horizontal axis through the ring, and a second vertical support arms attached to pivot about a fourth horizontal axis through the second rocking attachment block. A first tool is removably attached to the first vertical support arm and has distal and proximal sections which are aligned along an axis passing through an intersection of the first and second horizontal axes. A second tool is removably attached to the second vertical support arm and has distal and proximal sections which are aligned along an axis passing through the intersection of the third and fourth horizontal axes.

In specific embodiments, the first and second rocking attachment blocks are connected to the exterior periphery of the ring. Such exterior attachment is a particular advantage as it reduces the structure that occupies the central opening of the ring. In particular, by removably attaching the tools to the upper ends of the arms, only the mid-portions will pass through the central opening of the ring or other support frame. The first and third horizontally axes are usually axially aligned and the first and second rocking attachment blocks are usually on opposite sides of the ring. The first and second vertical support arms are typically attached to the first and second rocking attachment blocks, respectively, and the second and fourth horizontal axes are parallel but spaced horizontally apart from each other.

In further specific embodiments, each tool preferably has a semi-circular mid-portion which passes through the central opening of the ring, wherein the midsections are positioned to avoid interference as the tools are independently pivoted about all four horizontal axes, and at least one tool usually comprises an effector at a distal end thereof, an actuator at a proximal end thereof, and core passing therethrough which mechanically couples the actuator to the effector. The core is typically translatable within said seal at least one tool so that the actuator may be extended and retracted relative to the mid-portion to extend and retract the effector, and the distal and proximal sections are configured to telescope to accommodate extension and retraction of the actuator and effector.

The tool movement can be broken down into three specific types: (1) up/down or pivotal about a first horizontal axis, (2) medial/lateral or pivotal about a second horizontal axis orthogonal to the first horizontal axis, and (3) in/out in an axial direction through the tool. During medial and lateral movement of the tool, the semicircular segment moves along the circumference of a virtual circle where the attached arm is pivoted at the center of this circle. This mechanism assures that the distance of both tools within the umbilicus will not change during the medial and lateral displacement of the handle/effector. During the in/out movement.

In a third aspect of the present invention, methods for performing laparoscopic surgery through a single port comprise securing a frame having a central opening over an incision in a patient's abdomen to define the single port. A first tool is attached to a first pivotal attachment element at a first location on an outer periphery of the frame, and a second tool is attached to a second pivotal attachment element at a second location on the outer periphery of the frame. Each tool has distal and proximal sections which lie on axes passing through the pivotal attachment elements and mid-portions which remain positioned within the central opening of the frame but avoid interference as the tools are manipulated by a user during a surgery.

In specific embodiments of the methods, one of the first and second tools detached from the pivotal attachment element, and a third tool is attached to the respective pivotal attachment element, wherein the third tool has distal and proximal sections which lie on an axis passing through the pivotal attachment element and a mid-portion which remains positioned within the central opening of the frame as the tools are manipulated by a user during the surgery. The proximal ends of the tools are typically manipulated to pivotally position the distal sections at desired locations within a surgical field, and the proximal ends of the tools may be axially extended and retracted to axially extend and retract the distal sections, typically to position an end effector at a desired location in the surgical field.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
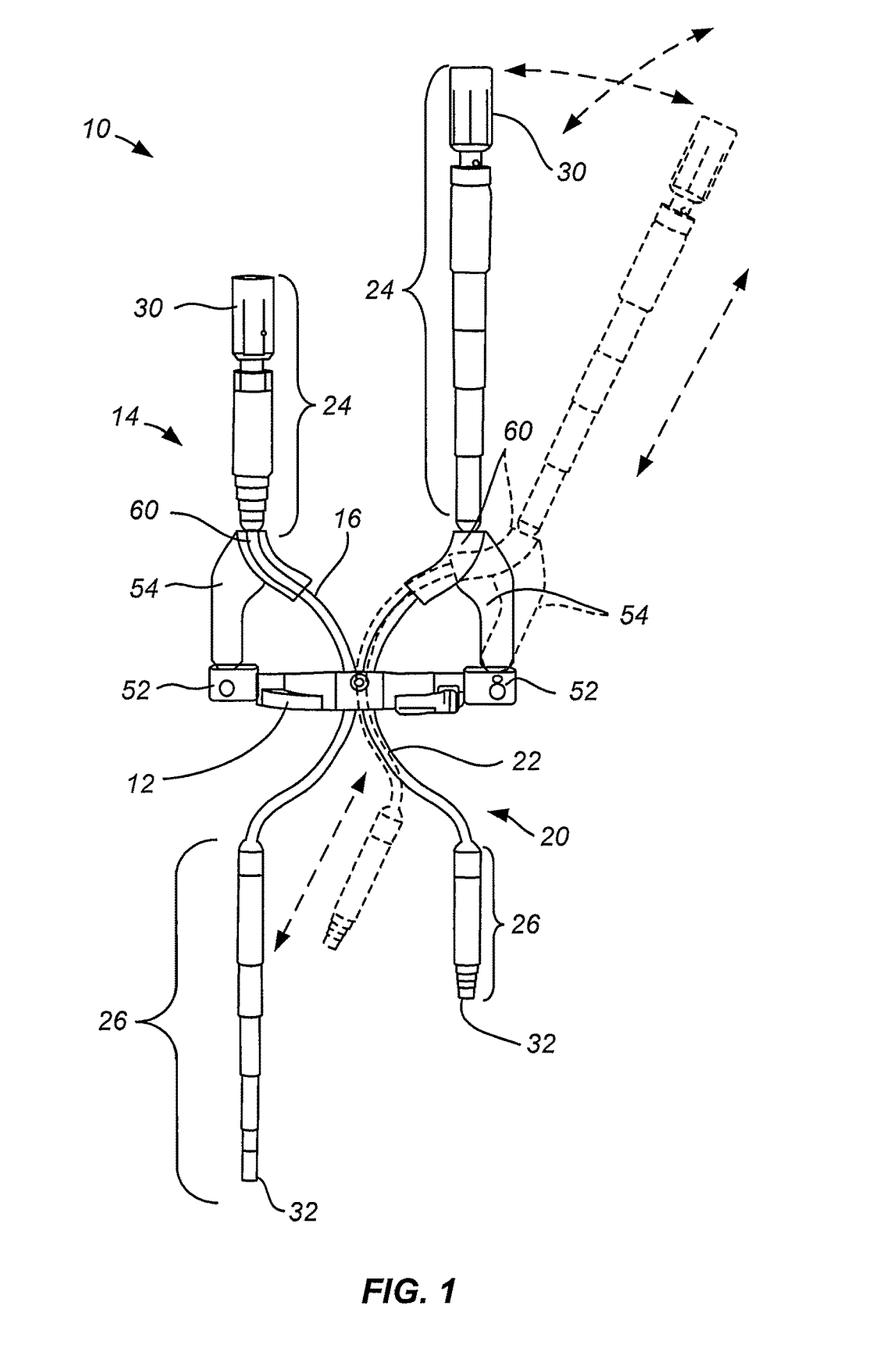
FIG. 1 is a side view of a system constructed in accordance with the principles of the present invention including first and second tools pivotally mounted to a support frame with a repositioned view of one of the tools shown in broken line.
Figure 2:
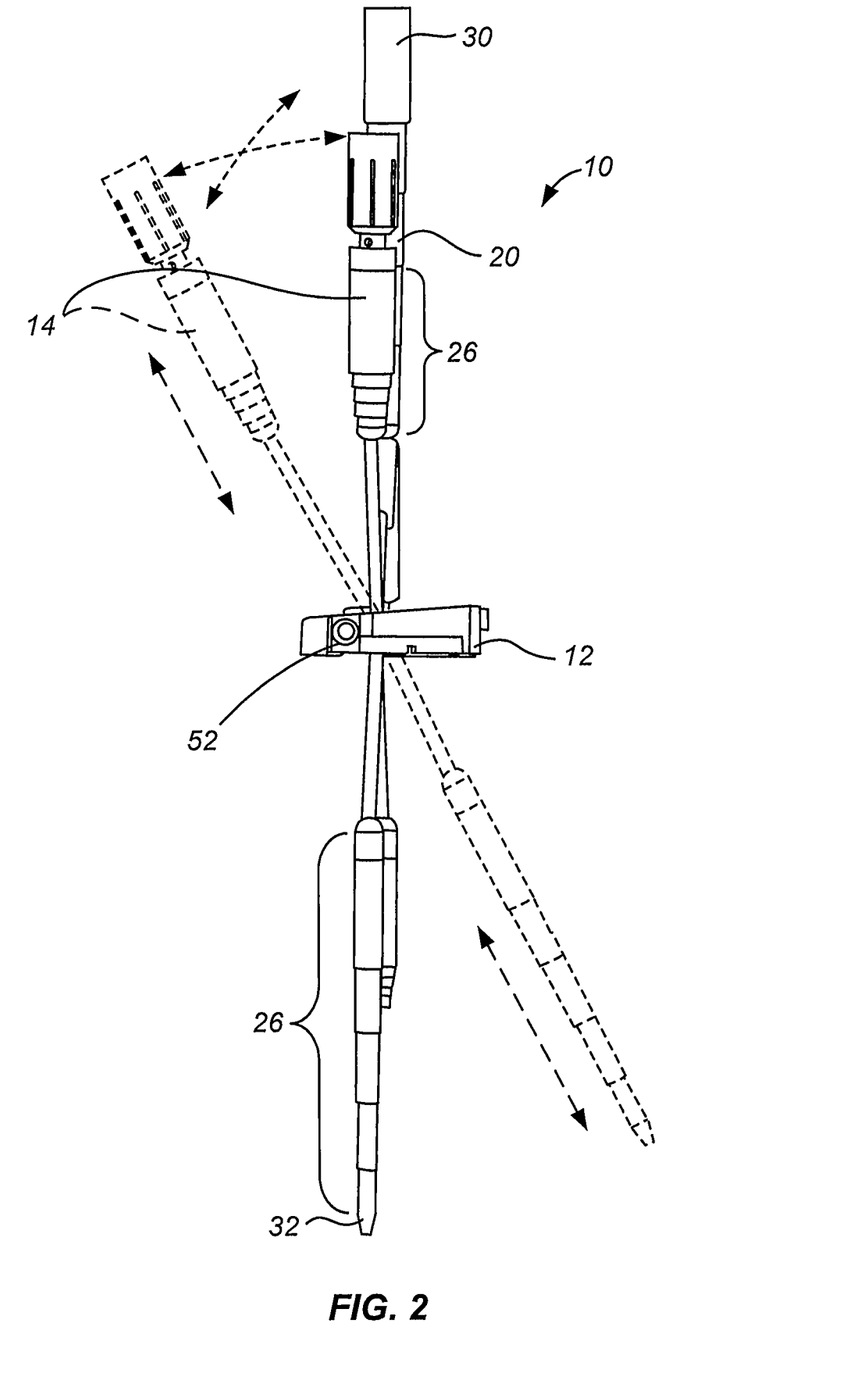
FIG. 2 is a side view of the system of FIG. 1.
Figure 7:
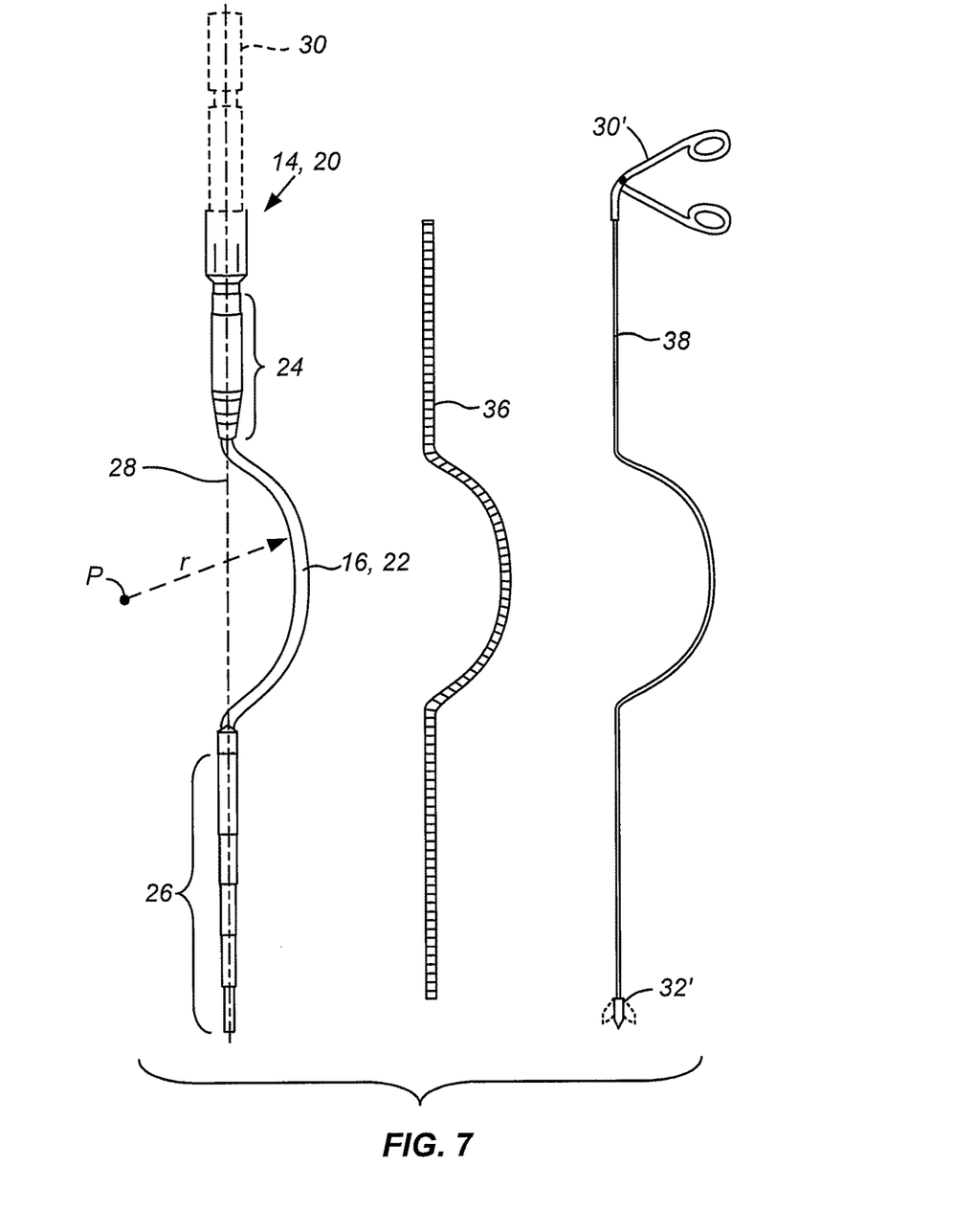
FIG. 7 is an exploded view of an exemplary embodiment of a tool useful in the laparoscopic tool system of the present invention.

Referring now to FIGS. 1 and 2, a laparoscopic tool system 10 constructed in accordance with the principles of the present invention comprises a tool attachment frame 12 having a first tool 14 and a second tool 20 pivotally attached thereto. The first tool has a mid-portion 16 and the second tool has a mid-portion 22, and both mid-portions extend generally inwardly from an axis 28 of the tool, as best illustrated in FIG. 7. Both mid-portions 16 and 22 are preferably circular and have a radius r emanating from a virtual rotation point p, which is also best seen in FIG. 7. The virtual rotation point p is generally aligned with a pivoting assembly attached to an outer periphery of the tool attachment frame 12, as will be described in more detail hereinbelow with reference to FIGS. 3, 4A and 4B. Having the virtual rotation points of each tool located outside the periphery of the ring allows the generally circular midportions 16 and 22 to pass and move through the central opening 18 of the frame 12 without interfering with each other. While the mid-portions 16 and 22 could alternatively have non-circular geometries which extend radially inward relative to the frame 12, for example being oval or polyhedral, the circular shape causes the passage point of the mid-portion to remain fixed within the central opening 18 of the frame so long as the tool is constrained to move in to orthogonal planes by the pivot attachment as will be explained in more detail hereinafter.

Each tool 14 and 20 includes a proximal section 24 and distal section 26. These proximal and distal sections are generally straight and lie along a common axis 28 (FIG. 7) which is generally not aligned with the virtual pivot point P. Thus, the mid-portions 16 and 22 of the tools 14 and 20 will generally circumscribe less than 180° of a full circle, typically circumscribing approximately 120°.

In preferred embodiments, both the proximal section 24 and the distal section 26 of each tool will have a telescoping configuration which allows axial extension and retraction of the tool during a procedure, as will be described in greater detail hereinafter with reference to FIG. 7.

Figure 3:
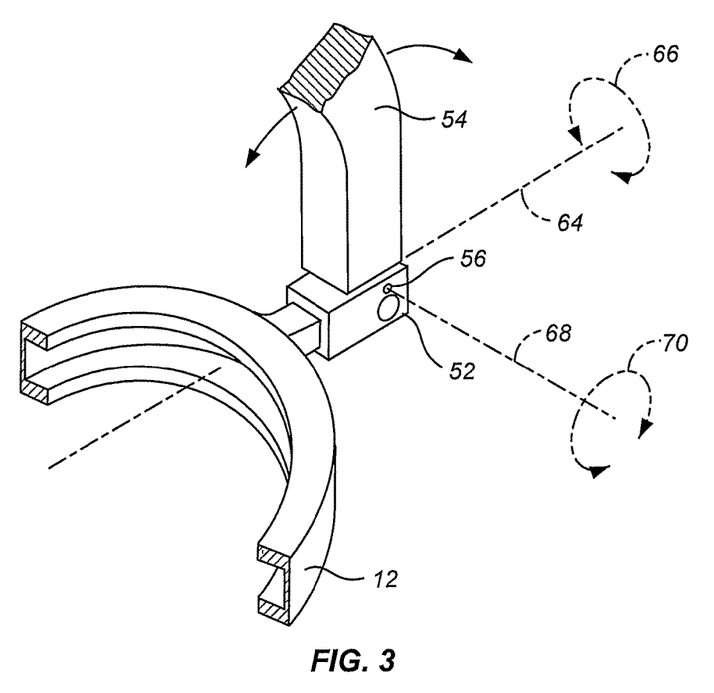
FIG. 3 is a detailed, perspective view illustrating the pivotal attachment of a rocking attachment block to the tool support frame and a second pivotal attachment point of a vertical support arm to the rocking attachment block.
Figure 4A:
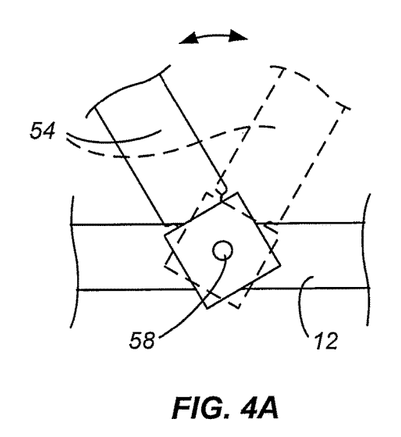
FIGS. 4A and 4B illustrate pivoting or rotation of the support arm in orthogonal planes relative to the tool attachment frame.
Figure 4B:
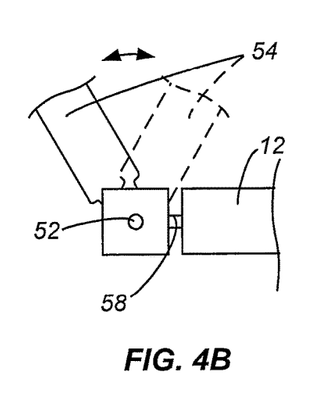

Referring now to FIGS. 3, 4A, and 4B, a rocking attachment block 52 is pivotally secured to the tool attachment frame 12 to rotate about a first axis 64, as shown in broken line. The rotational direction is shown by arrow 66. The pivot or rotation point 58 is best seen in FIGS. 4A and 4B.

A vertical support arm 54, in turn, is pivotally attached to the rocking attachment block 52 to pivot or rotate about a second axis 68, as shown by arrow 70. In this way, the vertical support arm 54 is able to pivot in two orthogonal planes relative to the vertical plane defined by the tool attachment plane 12. As mentioned previously, the constraint of the vertical support arm to pivot or rotate in two orthogonal planes limits movement of the circular mid-portions 16 and 22 of the first and second tools 14 and 20, respectively, so that they always pass through the same location within the circular opening 18 of the tool attachment frame 12. While it would also be possible to use a single, universal joint attaching the vertical support arm 54 to the tool attachment 12, the additional degrees of freedom of motion would allow the mid-portions of the tools to wobble side-to-side within the circular opening, thus increasing the chances of interference of the tools and unintended engagement of the inner periphery of the tool attachment frame 12. Referring again to FIGS. 4A and 4B, the motion of the vertical support arm 54 relative to axis 64 can be seen in broken line. Similarly, referring to FIG. 4B, the motion of vertical support arm 54 relative to the second axis 68 is seen in broken line.

Figure 5:
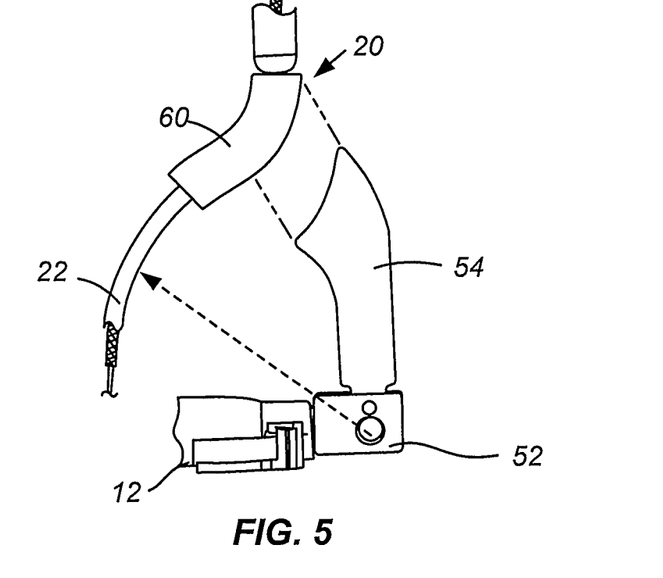
FIG. 5 is a detailed view illustrating the separability of a tool attachment block which forms part of each laparoscopic tool to the vertical support arm which is coupled to the tool support frame.

Referring now to FIG. 5, it will be desirable to exchange the tools during the performance of any particular laparoscopic procedure, and a variety of different tools will be available. Such interchangeability can be conveniently achieved by providing a tool attachment block 60 on each of the tools 14 and 20. Conveniently, the tool attachment block 60 may be attached toward the upper end of the mid-portion 22 so that the attachment point with the vertical support arm is raised vertically above the frame 12 by a maximum distance. By moving the attachment point vertically upward, the unencombered length of the mid-portion 16 or 22 is increased, allowing maximum rotation of the tool in and out of the central opening 18 of the support frame 12.

Figure 6:
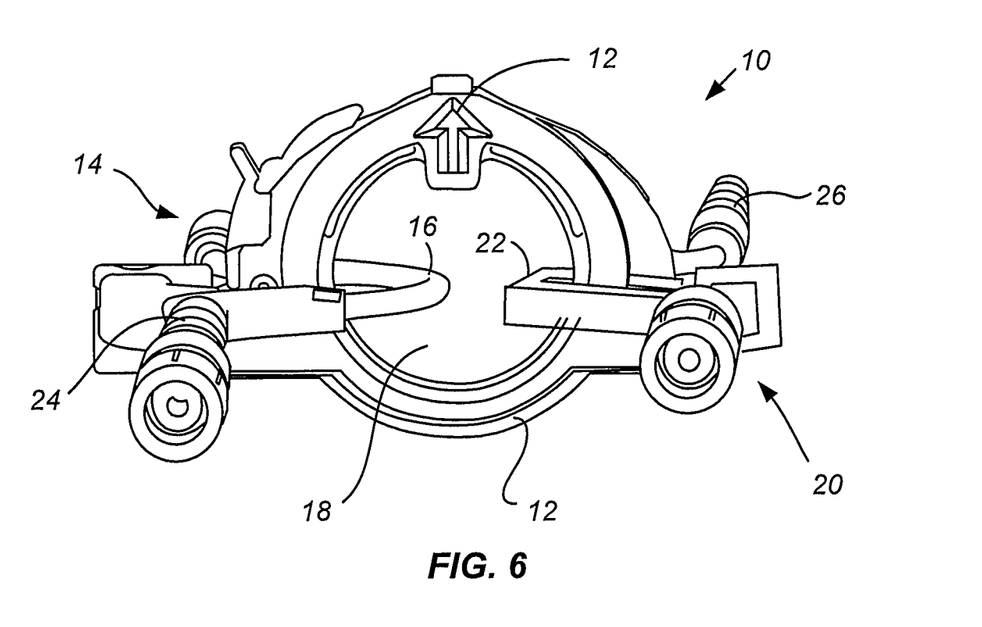
FIG. 6 is a top view of the laparoscopic tool system 10 of the present invention showing generally how a physician would view the system during use.

Referring now to FIG. 6, the tool support frame 12 is conveniently formed as a circular ring with a circular central opening 12. Conveniently, an arrow 72 or other indicator will allow a user to orient the tool system 10 relative to the target site within the abdomen or other body cavity to be treated. Conveniently, the arrow will be pointed directly at the target region so that the tools 14 and 16 are aligned along the line which is generally perpendicular to the direction toward the intended surgical site. In this way, the tools will be generally equidistant to the target site and manipulation of the tools will be more intuitive.

An exemplary construction of a tool 16, 22 is shown in FIG. 7. The tool of FIG. 7 will have forceps or other scissors-like end effector 32' which is actuated by a pivoting handle 30'. The handle 30' will operate by pulling pull wire 38 which passes through a central lumen of a flexible cable 36. The assembly of the flexible cable 36 and pull wire 38, in turn, is located within a luminar central passage of the tool 16/22. The length of the cable 36 will be fixed and will equal the length of the tool 16/22 with one of the telescoping hands fully extended and the other fully contracted. In this way, pushing and pulling on the actuator 30 relative to the mid-portion 16/22 of the tool will cause one of the telescoping sections to elongate while the other foreshortens. Each telescoping section, however, will be able to cover and maintain axial rigidity for the cable 36 and wire 38 so that the tool maintains alignment along the axis 38 (with the exception of the circular midsection). Such tool construction is generally described in U.S. patent publication 2012/0116362, the full text of which has been previously incorporated herein by reference.

It should be noted, however, that the present invention can accommodate a wide variety of more and less complicated laparoscopic tools. For example, simple electrocaudiry tools may be provided having the axial geometry with offset circular midsection, as shown in all previous figures. There would be no need to provide any core, however, as a simple electrical conductor can be utilized within the interior of the tool in order to extend and retract the tool as just described. Other tool configurations will also be capable of being implemented within the systems of the present invention.

Figure 8:
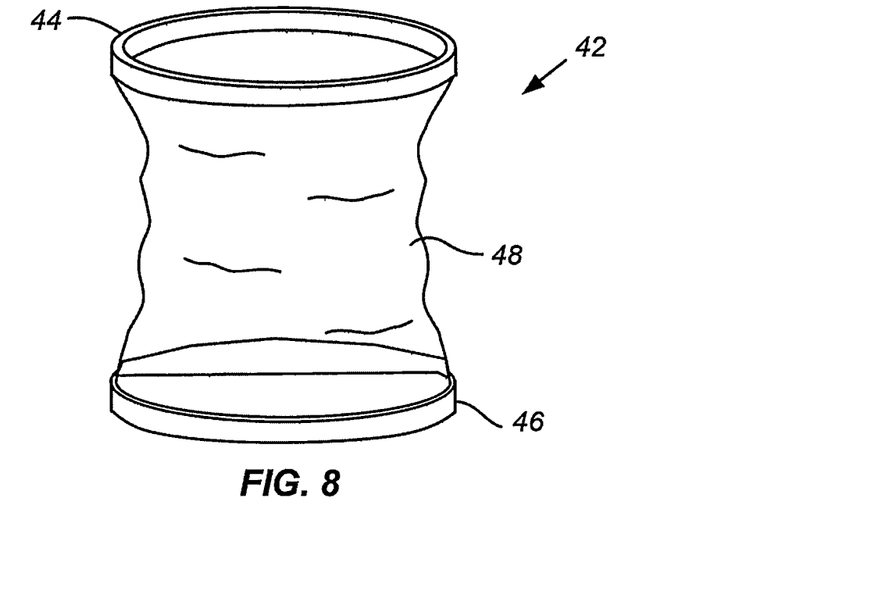
FIG. 8 illustrates a transcutaneous seal which is useful for attachment of the laparoscopic tool system of the present invention.
Figure 9:
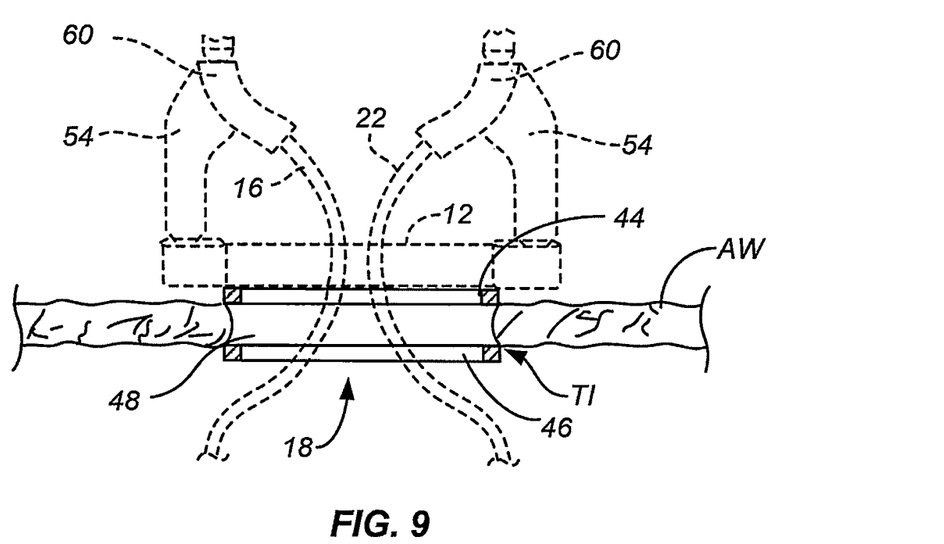
FIG. 9 illustrates the transcutaneous seal of FIG. 8 in place through an incision in a patient's umbilicus further illustrating attachment of the laparoscopic tool system in broken line.

Referring now to FIG. 8, a transcutaneous seal 42 comprises an upper for ring 44 and a lower end or ring 46. A flexible sheath 48 extends between the upper and lower ends. The seal may be disposed in a transcutaneous incision TI through and abdominal wall AW, as shown in FIG. 9. Conveniently, the sheath 48 may be generally elastic, and the length of the sheath may be adjusted by rolling the sheath over either the upper or lower rings, allowing the transcutaneous seal to be stretched and placed over the transcutaneous insertion TI.

As shown in FIG. 9, once in place, the tool attachment frame 12 may be attached to the upper end or ring 44 of the transcutaneous seal 42, thus fixing the frame in place relative to the patient. The tools 14 and 20 may then be attached to the vertical support arms 54 and the tools then used to perform a laparoscopic procedure by manipulating the proximal ends of the tools to reposition the distal ends where desired. As the procedure progresses, the tools may be interchanged for other tools by simply detaching the tool attachment blocks 60 from the vertical support arms 54.

What is claimed is:

1. A laparoscopic tool system comprising:
    a frame having a periphery and a central opening in a horizontal plane, said frame being configured to lie over a transcutaneous incision;
    a first tool support arm pivotally attached to an exterior of the frame by a first pivotal attachment assembly located at a first location on the frame, wherein said first pivotal attachment assembly includes a first pivot in the horizontal plane and a second pivot in the horizontal plane, wherein the first and second pivots are oriented orthogonally with respect to each other so that movement of the first tool support arm is completely constrained within first and second orthogonally oriented vertical planes and wherein a mid-portion of a first tool supported by the first tool support arm passes through the central opening of the frame; and
    a second tool support arm pivotally attached to an exterior of the frame by a second pivotal attachment assembly located at a second location on the frame, wherein said second pivotal attachment assembly includes a first pivot in the horizontal plane and a second pivot in the horizontal plane, wherein the first and second pivots are oriented orthogonally with respect to each other so that movement of the second tool support arm is completely constrained within first and second orthogonally oriented vertical planes and wherein a mid-portion of a second tool supported by the second tool support arm passes through the central opening of the frame;
    wherein interference between the first. and second tools as the tools are pivoted in said two vertical planes is avoided.

2. A system as in claim 1, wherein the frame comprises a circular ring.

3. A system as in claim 1, further comprising the first and second tools' wherein the first tool support arm and the second tool support arm are configured so that each tool has proximal and distal sections that lie along a common axis which passes outside the periphery of the frame.

4. A system as in claim 3, wherein the distal and proximal sections are configured to telescope to accommodate extension and retraction of an actuator and an effector.

5. A system as in claim 3, wherein the mid-portion of the first tool and the mid-portion of the second tool are each semi-circular and each extend radially inwardly from the common axis of the proximal and distal sections.

6. A system as in claim 3, wherein at least one of said first and second tools comprises an effector at a distal end thereof, an actuator at a proximal end thereof, and a core passing therethrough which mechanically couples the actuator to the effector.

7. A system as in claim 6, wherein the core is translatable within said at least one of said first and second tools so that the actuator may be extended and retracted relative to the mid-portion of said at least one of said first and second tools to extend and retract the effector of said at least one of said first and second tools.

8. A laparoscopic tool system comprising:
    a transcutaneous incision seal having one end configured to reside on an interior side of an incision, a second end configured to reside on an exterior side of the incision, and sheath extending between the ends to protect the incision;
    a ring having a central opening, a lower surface, and an exterior periphery, wherein the lower surface is configured to removably attach to the second end of the transcutaneous incision seal;
    a first rocking attachment block pivotally attached to the ring to pivot about a first horizontal axis through a plane of the ring, wherein said first rocking attachment block extends radially outwardly from a first location on the external periphery of the ring;
    a first vertical support arm pivotally attached to the first rocking attachment block to pivot about a second horizontal axis through the first rocking attachment block, wherein the second horizontal axis is orthogonal to the first horizontal axis;
    a second rocking attachment block attached to the ring to pivot about a third horizontal axis through a plane of the ring, wherein said second rocking attachment block extends radially outwardly from a second location on the external periphery of the ring;
    a second vertical support arm pivotally attached to the second rocking attachment block to pivot about a fourth horizontal axis through the second rocking attachment block, wherein the fourth horizontal axis is orthogonal to the third horizontal axis;
    a first tool removably attached to the first vertical support arm, said first tool having distal and proximal sections which are aligned along an axis passing through an intersection of the first and second horizontal axes; and
    a second tool removably attached to the second vertical support arm, said second tool having distal and proximal sections which are aligned along an axis passing through the intersection of the third and fourth horizontal axes.

9. A system as in claim 8, wherein the first and second rocking attachment blocks are connected to the exterior periphery of the ring.

10. A system as in claim 9, wherein the first and third horizontal axes are axially aligned and the first and second rocking attachment blocks are on opposite sides of the ring.

11. A system as in claim 10, wherein the first and second vertical support arms are attached to the first and second rocking attachment blocks, respectively, and the second and fourth horizontal axes are parallel but spaced horizontally apart from each other.

12. A system as in claim 11, wherein each tool has a semi-circular mid-portion which passes through the central opening of the ring, wherein the mid-portions are positioned to avoid interference as the tools are independently pivoted about all four horizontal axes.

13. A system as in claim 8, wherein at least one of the first and second tools comprises an effector at a distal end thereof, an actuator at a proximal end thereof, and a core passing therethrough which mechanically couples the actuator to the effector.

14. A system as in claim 13, wherein the core of said at least one of the first and second tools is translatable within said seal so that the actuator of said at least one of the first and second tools may be extended and retracted relative to a mid-portion of said at least one of the first and second tools to extend and retract the effector of said at least one of the first and second tools.

15. A system as in claim 14, wherein the distal and proximal sections are configured to telescope to accommodate extension and retraction of the actuator and effector.

16. A method for performing laparoscopic surgery through a single port, said method comprising:
    securing a frame having a central opening over an incision in a patient's abdomen to define the single port;
    attaching a first tool to a first tool pivotal attachment assembly facing radially outwardly from a first location on an outer periphery of the frame;

attaching a second tool to a second tool pivotal attachment assembly facing radially outwardly from a second location on the outer periphery of the frame;

wherein movement of each tool is constrained by each respective tool pivotal attachment assembly to lie on an axis passing through a virtual rotation point defined by the pivotal attachment assemblies to remain positioned within the central opening of the frame but avoid interference as the tools are manipulated by a user during a surgery.

17. A method as in claim 16, further comprising detaching one of the first and second tools and attaching a third tool to the respective pivotal attachment assembly, wherein the third tool has distal and proximal sections which lie on an axis passing through the pivotal attachment assembly and a mid-portion which remains positioned within the central opening of the frame as the tools are manipulated by a user during the surgery.

18. A method as in claim 16, further comprising manipulating proximal ends of the tools to pivotally position distal sections of the tools at desired locations within a surgical field.

19. A method as in claim 18, further comprising axially extending and retracting the proximal ends of the tools to axially extend and retract the distal sections.

* * * * *